(12) United States Patent
Xu et al.

(10) Patent No.: US 7,566,797 B2
(45) Date of Patent: Jul. 28, 2009

(54) METAL CARBOXYLATE SALT NUCLEATING OR CLARIFYING AGENT COMPOUNDS AND RELATED POLYMER COMPOSITIONS AND METHODS

(75) Inventors: Jiannong Xu, Spartanburg, SC (US); Jiang Li, Spartanburg, SC (US); John David O. Anderson, Moore, SC (US); Keith A. Keller, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 407 days.

(21) Appl. No.: 11/367,688

(22) Filed: Mar. 3, 2006

(65) Prior Publication Data

US 2007/0208116 A1 Sep. 6, 2007

(51) Int. Cl.
*C07F 3/00* (2006.01)
*C07F 7/10* (2006.01)

(52) U.S. Cl. ............... 556/133; 556/419; 562/502; 524/186

(58) Field of Classification Search ........... 556/133, 556/419; 562/502; 524/186
See application file for complete search history.

(56) References Cited

U.S. PATENT DOCUMENTS

| | | | | |
|---|---|---|---|---|
| 4,349,552 A | | 9/1982 | Takaya et al. | |
| 4,515,640 A | * | 5/1985 | Kaschig et al. | 106/287.25 |
| 5,342,868 A | | 8/1994 | Kimura et al. | 524/108 |
| 6,465,551 B1 | | 10/2002 | Zhao et al. | 524/284 |
| 6,562,890 B2 | | 5/2003 | Dotson | 524/396 |
| 6,936,650 B2 | | 8/2005 | Mannion et al. | 524/285 |
| 6,946,507 B2 | | 9/2005 | Mannion et al. | 524/285 |
| 6,995,202 B2 | | 2/2006 | Lake, Jr. et al. | 524/285 |
| 2002/0177642 A1 | | 11/2002 | Zhao et al. | |

OTHER PUBLICATIONS

Gaunt, M.J. et al. *Tetrahedron letters* 1999, 40, 1803-1806.
Jaeschke, G. et al. *J. Org. Chem.* 1998, 63, 1190-1197.
Koch, H. et al. *Monatshefte für Chemie* 1971, 102, 609-621.
Morgan, M.S. et al. *JACS* 1944, 66, 404-406.

* cited by examiner

*Primary Examiner*—Kriellion A Sanders
(74) *Attorney, Agent, or Firm*—Robert M. Lanning

(57) ABSTRACT

Nucleating agent compounds are used in polymers, such as polypropylene, to improve both the properties and processing characteristics of the polymer. Some nucleating agents may be used also as clarifiers to reduce the visual haze in finished polymeric articles, thereby increasing clarity of finished polymeric articles. Compounds of a carboxylate salt which employ a combination of an amide group and a metal cation salt perform well as nucleating agents, and provide substantial clarity benefits in a polymer. Other compounds of the invention may employ metal carboxylate salts in combination with an ester group. In other embodiments of the invention a dimer of such compounds may be employed.

7 Claims, No Drawings

METAL CARBOXYLATE SALT NUCLEATING OR CLARIFYING AGENT COMPOUNDS AND RELATED POLYMER COMPOSITIONS AND METHODS

BACKGROUND OF THE INVENTION

Nucleating agents may improve polymer properties in several ways. When used in polymers, such as polypropylene, nucleating agents may increase the rate of crystallization. Such nucleating agents may change the polymer crystallization temperature characteristics. This may provide benefits in polymer manufacturing processes, as well as the final aesthetics of polymer articles.

Injection molding polymer applications frequently use nucleating agents. Blow molding, sheet extrusion, and thermoforming applications also may benefit from their use. Nucleating agents may reduce cycle time by reducing the set-up time in the mold. However, care must be taken to ensure that shrinkage and impact properties are not negatively impacted.

The optical benefits of nucleating agents include increased clarity and improved gloss in finished polymeric articles. These properties may improve because of the dramatic increase in the number of fine crystals. When crystals are smaller than the wavelength of visible light, the light passing through the article is much less scattered, thereby haze is reduced when nucleating agents are used. When utilized to improve transparency in materials such as polypropylene, these materials are referred to as clarifiers, or clarifying agents.

Five major categories of nucleating agents include: substituted sorbitols, carboxylic acid salts such as sodium benzoate, low molecular weight polyolefins, ionomer resins, and organophosphate salts.

One nucleating agent marketed by Milliken & Company is known as HYPERFORM™, or HPN-68™, as shown in U.S. Pat. No. 6,465,551. This product, which comprises a dicarboxylate salt, is commonly known as "hyper" nucleating agent. It is commonly used in injection molded polypropylene. However, this product is not used widely as a clarifier in most instances, in part because a lack of adequate dispersion in the polymer does not provide sufficient optical clarity in finished articles.

Another nucleating agent marketed by Asahi Denka Corporation of Japan is NA-21™. The compound of this nucleating agent is disclosed in U.S. Pat. No. 5,342,868. This compound is mostly used as a clarifier, and does not provide adequate nucleation benefits to serve as a true nucleating agent for most polymer applications.

It is a significant challenge in the industry to locate compounds that are capable of affording both good nucleating ability and good optical clarity benefits in a polymer. There is a substantial need for agents that provide both nucleation benefits and clarity benefits when employed in polymer systems. This invention addresses that need.

DETAILED DESCRIPTION OF THE INVENTION

Reference now will be made to the embodiments of the invention, one or more examples of which are set forth below. Each example is provided by way of explanation of the invention, not as a limitation of the invention.

The invention relates to improved nucleating agent compounds, masterbatch compositions containing such nucleating compounds, and polymer compositions containing such compounds, and also methods for use of the same. Improved dispersion has been observed for compounds of this type in polymers, by the use of the compounds shown herein. Thus, the invention achieves good nucleation power (higher Tc values), and also improved optical performance (i.e. low haze) in most instances.

One approach employed in the practice of the invention is to use an amide group on one side of the molecule, as shown in Formula (I) below, and a metal carboxylate salt on the other side of the molecule. Yet another approach employs an ester group on one side of the molecule, with the metal carboxylate salt on the other side, as shown in Formula (II). In yet another approach, a half metal cation/half ester dimer compound may be employed, as shown in Formula (III). In general, these approaches facilitate the addition of a less polar group to the compound so as to improve the dispersion of the compound in polyolefins, such as polypropylene.

Compounds that may be effective in the application of the invention are not limited to only those shown herein, and shown in the examples and Tables 1-6 below. Many other compounds within the general scope of the compounds described may be imagined and employed by a person of skill in the art, and such other compounds are within the scope and spirit of the present invention.

In one application of the invention, a metal salt compound is employed,

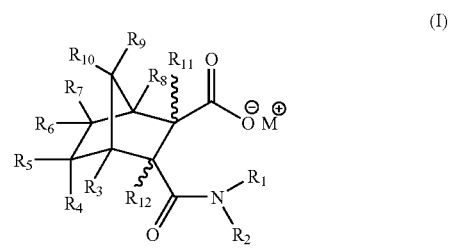

(I)

wherein M is a cation selected from the group consisting of proton, metal or organic cations, R1 and R2 are independently selected from the group consisting of hydrogen, C1-C30 alkyl, C1-C30 alkenyl, C1-C30 alkynyl, C1-C30 alkoxy, hydroxy, aryl, alkylaryl, arylalkyl, polyoxyalkyl, polyaminoalkyl, and alkylsilyl; R1 and R2 can also together form C2-C9 alkylene carbocyclic, or C2-C9 alkylene carbocyclic containing nitrogen and/or oxygen, and $R_3$, $R_4$, $R_5$, $R_6$, $R_7$, $R_8$, $R_9$, $R_{10}$, $R_{11}$, and $R_{12}$ are independently selected from the group consisting of hydrogen, $C_1$-$C_9$ alkyl, hydroxy, $C_1$-$C_9$ alkoxy, amine, $C_1$-$C_9$ alkylamine, halogen, alkylphenyl, phenyl, further wherein two vicinal or geminal $C_1$-$C_9$ alkyl groups may be combined to form a carbocyclic ring of up to six carbon atoms.

The metal salt may employ essentially any metal cation, such as sodium, calcium, lithium, zinc, aluminum, titanium, strontium, or others. Within the scope, zinc, group I and group II (in periodic table) metal cations are quite useful. Among them, sodium, calcium, potassium, zinc ions are also useful. M can also be a proton, or an organic cation such as a quaternary ammonium salt. In one application, $R_1$ and $R_2$ comprise independently selected from $C_1$-$C_{30}$ alkyl groups, such as hexyl, cyclohexyl, pentyl, butyl, propyl, ethyl, methyl, isobutyl, isopropyl, stearyl, and the like.

In another embodiment, a metal salt ester compound:

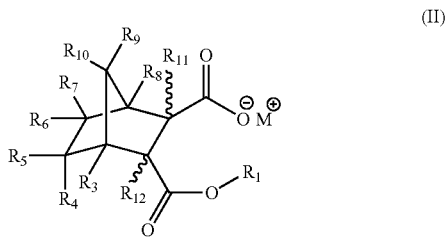

(II)

is disclosed, wherein M is a cation selected from the group consisting of proton, metal or organic cations, R1 is selected from the group consisting of hydrogen, C1-C30 alkyl, C1-C30 alkenyl, C1-C30 alkynyl, C1-C30 alkoxy, hydroxy, aryl, alkylaryl, arylalkyl, polyoxyalkyl, polyaminoalkyl, and alkylsilyl; and $R_3, R_4, R_5, R_6, R_7, R_8, R_9, R_{10}, R_{11},$ and $R_{12}$ are independently selected from the group consisting of hydrogen, $C_1$-$C_9$ alkyl, hydroxy, $C_1$-$C_9$ alkoxy, amine, $C_1$-$C_9$ alkylamine, halogen, alkylphenyl, phenyl, further wherein two vicinal or geminal $C_1$-$C_9$ alkyl groups may be combined to form a carbocyclic ring of up to six carbon atoms.

The metal salt may employ essentially any metal cation, such as sodium, calcium, lithium, zinc, aluminum, titanium, strontium, or others. Within the scope, zinc, group I and group II (in periodic table) metal cations are generally believed to be useful. Sodium, calcium, potassium, zinc ions can be used. M can also be a proton, or an organic cation such as a quaternary ammonium salt. In one application, $R_1$ comprises independently selected from $C_1$-$C_{30}$ alkyl groups, such as hexyl, cyclohexyl, pentyl, butyl, propyl, ethyl, methyl, isobutyl, isopropyl, stearyl, and the like. Among them, isopropyl and isobutyl are quite useful.

Furthermore, a dimer compound also may be practiced by way of the invention, as indicated below:

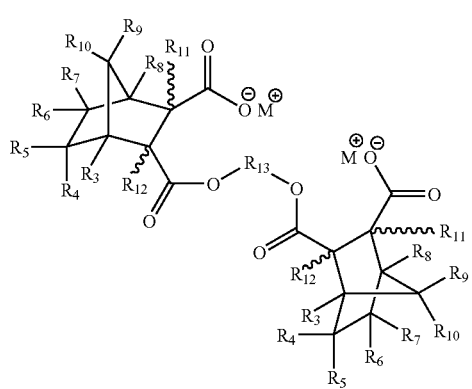

(III)

wherein M is a cation selected from the group consisting of proton, metal or organic cations, R13 is selected from the group consisting of C1-C30 alkylene, C1-C30 alkenylene, C1-C30 alkynylene, arylene, alkylarylene, arylalkylene, polyoxyalkylene, polyaminoalkylene, and alkylsilylene; and $R_3, R_4, R_5, R_6, R_7, R_8, R_9, R_{10}, R_{11},$ and $R_{12}$ are independently selected from the group consisting of hydrogen, $C_1$-$C_9$ alkyl, hydroxy, $C_1$-$C_9$ alkoxy, amine, $C_1$-$C_9$ alkyl amine, halogen, alkylphenyl, phenyl, further wherein two vicinal or geminal $C_1$-$C_9$ alkyl groups may be combined to form a carbocyclic ring of up to six carbon atoms.

The metal salt may employ essentially any metal cation, such as sodium, calcium, lithium, zinc, aluminum, titanium, strontium, or others. Within the scope, zinc, group I and group II (in periodic table) metal cations are believed to be quite useful. Among them, sodium, calcium, potassium, zinc ions may be employed. M can also be a proton, or an organic cation such as a quaternary ammonium salt. In one application, $R_{13}$ comprises independently selected from $C_1$-$C_{30}$ alkyl groups, such as hexylene, cyclohexylene, pentylene, butylene, propylene, ethylene, cyclohexane-1,4-diyldimethyl and the like. Among them, butylene and cyclohexane-1,4-diyldimethyl are particularly useful.

Each of the above compounds may be useful as applied into polyolefin resin. For purposes of this specification, the term polyolefin or polyolefin resin is intended to encompass any materials comprised of at least one semicrystalline polyolefin. Examples include isotactic and syndiotactic polypropylene, polyethylene, poly(4-methyl)pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Sometimes, the co-monomers, if present, will be provided in a minor amount, e.g., about 10 percent or less or even about 5 percent or less, based upon the weight of the polyolefin. Such co-monomers may serve to assist in clarity improvement of the polyolefin, or they may function to improve other properties of the polymer. Higher amounts of co-monomer (for instance, ethylene, e.g., 10-25% or more), may also be present in the polyolefin to impart greater impact resistance. Other polymers or rubber may also be compounded with the polyolefin. Other co-monomer examples include acrylic acid and vinyl acetate, and the like. Examples of olefin polymers whose transparency and crystallization temperature can be improved conveniently according to the present invention are polymers and copolymers of aliphatic mono-olefins containing 2 to about 6 carbon atoms which have an average molecular weight of from about 10,000 to about 2,000,000, preferably from about 30,000 to about 300,000, such as for example: polyethylene (PE), linear low density polyethylene (LLDPE), isotactic polypropylene (I-PP), syndiotactic polypropylene (s-PP), random copolymer polypropylene (RCP), crystalline ethylenepropylene copolymer (ICP), poly (1-butene), poly(4-methylpentene), poly(1-hexene), poly(1-octene), and poly(vinyl cyclohexene).

The polyolefins of the present invention may be described as basically linear, regular polymers that may optionally contain side chains such as are found in conventional low density polyethylene. Although polyolefins are quite useful in the practice of the invention, the nucleating agents of the present invention are not restricted to use in polyolefins, and may also give beneficial nucleation properties to polymers such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some degree of crystalline content may be improved with the nucleating agents of the present invention.

The compositions of the present invention may be obtained by adding the inventive salt as defined (or combination of salts or composition comprising such salts) to the thermoplastic polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

The nucleated thermoplastic is intended to be utilized as, for instance and not by limitation, medical devices, such as pre-filled syringes for retort applications, intravenous supply containers, and blood collection devices; food packages; liquid containers, such as for drinks, medicines, shampoos, and the like; apparel cases; microwaveable articles; shelves; cabinet doors; mechanical parts; automobile parts; sheet; pipes and tubes; rotationally molded products; blow-molded products; fiber (spun or nonwoven); compression molded products; basically any thermoplastic article wherein the effects of nucleation may be advantageous.

EXAMPLE 1

3-diisobutylcarbamoyl-bicyclo[2.2.1]heptane-2-carboxylic acid 41.5 g (0.25 mol) bicyclo[2.2.1]heptane dicarboxylic anhydride was charged and dissolved in 500 ml chloroform in a 1 L round bottom flask at room temperature using magnetic stirring. 32.3 g (0.25 mol) diisobutylamine was added to the system slowly using a syringe at room temperature. The reaction was allowed to go on for 16 hours at room temperature. The solvent was then removed by rotary evaporator. The white solid was dried and grounded. The product was characterized using FTIR and GC-MS. The yield was quantitative.

EXAMPLE 2

Sodium, 3-diisobutylcarbamoyl-bicyclo[2.2.1]heptane-2-carboxylate 29.5 g (0.1 mol) of diisobutylcarbamoyl-bicyclo[2.2.1]heptane-2-carboxylic acid (from example 1) was charged in a mixture of 200 ml water and 200 ml methanol. To this solution, a NaOH water solution was used to titrate until pH reaches about 10. Solvent was then removed using rotary evaporator. The white solid was then dried and grounded. The yield was quantitative.

EXAMPLE 3 calcium, 3-diisobutylcarbamoyl-bicyclo[2.2.1]heptane-2-carboxylate 15.8 g (0.05 mol) of sodium, diisobutylcarbamoyl-bicyclo[2.2.1]heptane-2-carboxylate (from example 2) was charged in a mixture of 200 ml water and 200 ml methanol. To this solution, a calcium chloride water solution (made of 100 ml of water and 3.7 g (0.025 mol) $CaCl_2.2H_2O$) was added. The mixture was then allowed to stir at room temperature for 2 hours. The white solid was then filtered, dried and grounded. The yield was quantitative.

EXAMPLE 4

Zinc, 3-diisobutylcarbamoyl-bicyclo[2.2.1]heptane-2-carboxylate 15.8 g (0.05 mol) of sodium, diisobutylcarbamoyl-bicyclo[2.2.1]heptane-2-carboxylate (from example 2) was charged in a mixture of 200 ml water and 200 ml methanol. To this solution, a zinc sulfate water solution (made of 100 ml of water and 7.2 g (0.025 mol) $ZnSO_4.7H_2O$) was added. The mixture was then allowed to stir at room temperature for 2 hours. The white solid was then filtered, dried and grounded. The yield was quantitative.

EXAMPLE 5

Sodium, 3-piperidinecarbamoyl-bicyclo[2.2.1]heptane-2-carboxylate 41.5 g (0.25 mol) bicyclo[2.2.1]heptane dicarboxylic anhydride was charged and dissolved in 500 ml chloroform in a 1 L round bottom flask at room temperature using magnetic stirring. 21.5 g (0.25 mol) piperidine was added to the system slowly using a syringe at room temperature. The reaction was allowed to go on for 48 hours at room temperature. White precipitate appeared and was filtered. The precipitate was further dried, and it was then introduced to a mixture of water (200 ml) and methanol (200 ml). To this system, a NaOH water solution was used to titrate until pH reaches about 10. Solvent was then removed using rotary evaporator. The white solid was dried and grounded. The product was characterized using FTIR and GC-MS. The yield is 75%.

EXAMPLE 6

Sodium, 3-morpholinecarbamoyl-bicyclo[2.2.1]heptane-2-carboxylate 41.5 g (0.25 mol) bicyclo[2.2.1]heptane dicarboxylic anhydride was charged and dissolved in 500 ml chloroform in a 1 L round bottom flask at room temperature using magnetic stirring. 21.7 g (0.25 mol) morpholine was added to the system slowly using a syringe at room temperature. The reaction was allowed to go on for 48 hours at room temperature. White precipitate appeared and was filtered. The precipitate was further dried, and it was then introduced to a mixture of water (200 ml) and methanol (200 ml). To this system, a NaOH water solution was used to titrate until pH reaches about 10. Solvent was then removed using rotary evaporator. The white solid was dried and grounded. The product was characterized using FTIR and GC-MS. The yield was 85%.

EXAMPLE 7

Sodium, 3-dicyclohexylcarbamoyl-bicyclo[2.2.1]heptane-2-carboxylate 33.2 g (0.2 mol) bicyclo[2.2.1]heptane dicarboxylic anhydride was charged and dissolved in 300 ml chloroform in a 1 L round bottom flask at room temperature using magnetic stirring. 36.2 g (0.2 mol) dicyclohexylamine was added to the system slowly using a syringe at room temperature. The reaction was allowed to go on for 16 hours at room temperature. White precipitate appeared and was filtered. The precipitate was then charged to chloroform, HCl/water solution (contains 0.2 mol HCl) was added. The system was fully stirred and allowed to phase separate. White solid was obtained from the chloroform layer when the solvent was removed using rotary evaporator. It was then introduced to a mixture of water (200 ml) and methanol (200 ml). To this system, a NaOH water solution was used to titrate until pH reaches about 10. Solvent was then removed using rotary evaporator. The white solid was dried and grounded. The product was characterized using FTIR and GC-MS. The yield was 50%.

EXAMPLE 8

Sodium, 3-N-ethylbenzylcarbamoyl-bicyclo[2.2.1]heptane-2-carboxylate 33.2 g (0.2 mol) bicyclo[2.2.1]heptane dicarboxylic anhydride and 27.0 g (0.2 mol) N-ethylbenzylamine were charged to 50 ml chloroform and 200 ml cyclohexane in a 1 L round bottom flask at room temperature. The reaction was allowed for 16 hours using magnetic stirring at room temperature. Solvent was stripped to give a white powder. It was then introduced to methanol (200 ml). To this system, a NaOH water solution was used to titrate until pH reaches about 10. Solvent was then removed using rotary evaporator. The solid was washed using acetone, dried and grounded. The product was characterized using FTIR and GC-MS. The yield was quantitative.

EXAMPLE 9

Sodium, 3-N-ethylcyclohexylcarbamoyl-bicyclo[2.2.1]heptane-2-carboxylate 33.2 g (0.2 mol) bicyclo[2.2.1]heptane dicarboxylic anhydride and 25.4 g (0.2 mol) N-ethylcyclohexylamine were charged to 50 ml chloroform and 200 ml cyclohexane in a 1 L round bottom flask at room temperature. The reaction was allowed for 16 hours using magnetic stirring at room temperature. Solvent was stripped to give a white powder. It was then introduced to methanol (200 ml). To this system, a NaOH water solution was used to titrate until pH reaches about 10. Solvent was then removed using rotary evaporator. The solid was washed using acetone, dried and grounded. The product was characterized using FTIR and GC-MS. The yield was quantitative.

EXAMPLE 10

Sodium, 3-dipentylcarbamoyl-bicyclo[2.2.1]heptane-2-carboxylate 41.5 g (0.25 mol) bicyclo[2.2.1]heptane dicarboxylic anhydride was charged and dissolved in 500 ml chloroform in a 1 L round bottom flask at room temperature using magnetic stirring. 39.3 g (0.25 mol) dipentylamine was added to the system slowly using a syringe at room temperature. The reaction was allowed to go on for 16 hours at room temperature. The solvent was then removed by rotary evaporator. The white solid was then introduced to a mixture of water (200 ml) and methanol (200 ml). To this system, a NaOH water solution was used to titrate until pH reaches about 10. Solvent was then removed using rotary evaporator. The white solid was dried and grounded. The product was characterized using FTIR and GC-MS. The yield was quantitative.

EXAMPLE 11

3-(isobutyloxy)-bicyclo[2.2.1]heptane-2-carboxylic acid 33.2 g (0.2 mol) bicyclo[2.2.1]heptane dicarboxylic anhydride was charged to 300 ml isobutyl alcohol in a 1 L round bottom flask. The system was refluxed for 2 hours with magnetic stirring. The solvent was then removed by rotary evaporator. The system was then dried and grounded. The product was characterized using FTIR and GC-MS. The yield was quantitative.

EXAMPLE 12

Sodium, 3-(isobutyloxy)-bicyclo[2.2.1]heptane-2-carboxylate 24.0 g (0.1 mol) of 3-(isobutyloxy)-bicyclo[2.2.1]heptane-2-carboxylic acid (from example 11) was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

EXAMPLE 13 calcium, 3-(isobutyloxy)-bicyclo[2.2.1]heptane-2-carboxylate 26.2 g (0.1 mol) of sodium, 3-(isobutyloxy)-bicyclo[2.2.1]heptane-2-carboxylic acid (from example 12) was dissolved in 200 ml water. To this solution, a 150 ml water solution containing 7.4 g (0.05 mol) CaCl2.2H2O was added. White precipitate was observed. Filtration was used to collect the white precipitate, which was then dried and grounded. The product was characterized using FTIR and GC-MS. The yield was quantitative.

EXAMPLE 14 zinc, 3-(isobutyloxy)-bicyclo[2.2.1]heptane-2-carboxylate 26.2 g (0.1 mol) of sodium, 3-(isobutyloxy)-bicyclo[2.2.1]heptane-2-carboxylic acid (from example 12) was dissolved in 200 ml water. To this solution, a 150 ml water solution containing 14.3 g (0.05 mol) ZnSO4.7H2O was added. White precipitate was observed. Filtration was used to collect the white precipitate, which was then dried and grounded. The product was characterized using FTIR and GC-MS. The yield was quantitative.

EXAMPLE 15

Sodium, 3-(n-butyloxy)-bicyclo[2.2.1]heptane-2-carboxylate 33.2 g (0.2 mol) bicyclo[2.2.1]heptane dicarboxylic anhydride was charged to 300 ml n-butyl alcohol in a 1 L round bottom flask. The system was refluxed for 2 hours with magnetic stirring. The solvent was then removed by rotary evaporator. The system was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

EXAMPLE 16

Sodium, 3-(n-propyloxy)-bicyclo[2.2.1]heptane-2-carboxylate 33.2 g (0.2 mol) bicyclo[2.2.1]heptane dicarboxylic anhydride was charged to 300 ml n-propyl alcohol in a 1 L round bottom flask. The system was refluxed for 2 hours with magnetic stirring. The solvent was then removed by rotary evaporator. The system was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield is quantitative.

EXAMPLE 17

3-(benzyloxy)-bicyclo[2.2.1]heptane-2-carboxylic acid 33.2 g (0.2 mol) bicyclo[2.2.1]heptane dicarboxylic anhydride and 27 g (0.25 mol) benzyl alcohol were charged to 500 ml chloroform in a 1 L round bottom flask. The system was refluxed for 16 hours with magnetic stirring. The solvent was then removed by rotary evaporator. The solid was then dried and grounded. The product was characterized using FTIR and GC-MS. The yield was quantitative.

EXAMPLE 18

Sodium, 3-(2-ethyl-1-hexyloxy)-bicyclo[2.2.1]heptane-2-carboxylate 33.2 g (0.2 mol) bicyclo[2.2.1]heptane dicarboxylic anhydride and 32.5 g (0.25 mol) 2-ethyl-1-hexanol were charged to 500 ml chloroform in a 1 L round bottom flask. The system was refluxed for 16 hours with magnetic stirring. The solvent was then removed by rotary evaporator. The solid was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

EXAMPLE 19

Sodium, 3-(3-trimethylsilyl-1-propyloxy)-bicyclo[2.2.1]heptane-2-carboxylate 33.2 g (0.2 mol) bicyclo[2.2.1]heptane dicarboxylic anhydride and 33 g (0.25 mol) 3-trimethylsilyl-1-propanol were charged to 500 ml chloroform in a 1 L round bottom flask. The system was refluxed for 16 hours with magnetic stirring. The solvent was then removed by rotary evaporator. The solid was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

EXAMPLE 20

Sodium, 3-(stearyloxy)-bicyclo[2.2.1]heptane-2-carboxylate 33.2 g (0.2 mol) bicyclo[2.2.1]heptane dicarboxylic anhydride and 66 g (0.25 mol) stearyl alcohol were charged to 500 ml chloroform in a 1 L round bottom flask. The system was refluxed for 16 hours with magnetic stirring. The solvent was then removed by rotary evaporator. The solid was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

EXAMPLE 21

Structure as follows was made:

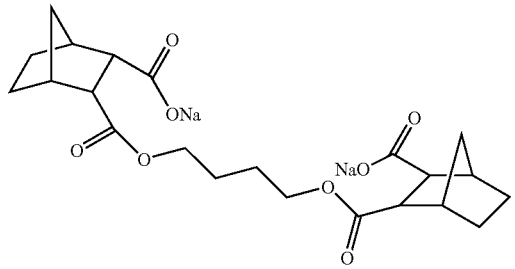

33.2 g (0.2 mol) bicyclo[2.2.1]heptane dicarboxylic anhydride and 9.0 g (0.1 mol) 1,4-butanediol were charged to 500 ml chloroform in a 1 L round bottom flask. The system was refluxed for 16 hours with magnetic stirring. The solvent was then removed by rotary evaporator. The solid was charged in a mixture of 200 ml water and 200 ml methanol. To this solution, a NaOH water solution was used to titrate until pH reaches about 10. Solvent was then removed using rotary evaporator. The product was characterized using FTIR and GC-MS. The white solid was then dried and grounded. The yield was quantitative.

EXAMPLE 22

Structure as follows was made:

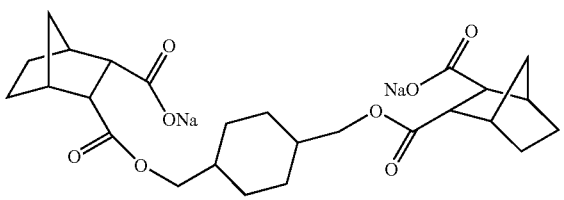

33.2 g (0.2 mol) bicyclo[2.2.1]heptane dicarboxylic anhydride and 14.4 g (0.1 mol) 1,4-cyclohexanedimethanol were charged to 500 ml chloroform in a 1 L round bottom flask. The system was refluxed for 16 hours with magnetic stirring. The solvent was then removed by rotary evaporator. The solid was charged in a mixture of 200 ml water and 200 ml methanol. To this solution, a NaOH water solution was used to titrate until pH reaches about 10. Solvent was then removed using rotary evaporator. The white solid was then dried and grounded. The product was characterized using FTIR and GC-MS. The yield was quantitative.

Sodium, bicyclo[2.2.1]heptane dicarboxylate, the comparative example, was obtained from Milliken Chemical under the trade name Hyperform® HPN-68.

Clarification and Nucleation Efficacy Test:

Thermoplastic compositions (plaques) were produced comprising the additives from the Examples above, and sample random copolymer polypropylene (RCP) resin plaques, produced by dry blended in a Henschel mixer at ~1600 rpm, extruded through a single screw extruder at 400-450° F., and pelletized. Accordingly, one kilogram batches of target polypropylene were produced in accordance with the following table:

TABLE 1

Random Copolymer Polypropylene Composition

| Component | Amount |
|---|---|
| Polypropylene random copolymer (Himont Profax ® SA849) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Nucleator | as noted |

The base RCP (having a density of about 0.9 g/cc, a melt flow of about 12 g/10 min) and all additives were weighed and then blended in a Henschel mixer for 1 minute at about 1600 rpm. All samples were then melt compounded on a Deltaplast single screw extruder at a ramped temperature from about 204° to 232° C. through four heating zones. The melt temperature upon exit of the extruder die was about 246° C. Upon melting the molten polymer was filtered through a 60 mesh (250 micron) screen. Plaques of the target polypropylene were then made through extrusion into an Arburg 25 ton injection molder. The molder was set at a temperature anywhere between 190 and 260° C., with a range of 190 to 240° C. preferred, most preferably from about 200 to 230° C. The plaques had dimensions of about 51 mm×76 mm×1.27 mm, and the mold had a mirror finish which was transferred to the individual plaques. The mold cooling circulating water was controlled at a temperature of about 25° C.

Testing for clarification and nucleating effects and other important criteria were accomplished through the formation of plaques of clarified polypropylene thermoplastic resin. These plaques were formed through the process outlined above with the specific compositions listed in the above Table 1.

These plaque formulations are, of course, useful embodiments of the inventive article and method and are not intended to limit the scope of this invention. The resultant plaques were then tested for peak crystallization temperatures (by Differential Scanning Calorimetry). Crystallization is important to determine the time needed to form a solid article from the molten polyolefin composition. To reduce the amount of time needed to form the final product, as well as to provide the most effective nucleation for the polyolefin, the best nucleator compound added will invariably also provide the highest crystallization temperature for the final polyolefin product. The nucleation composition efficacy, particular polymer peak crystallization temperature ($T_c$), was evaluated by using DSC according to ASTM D-794-85. To measure these temperatures, the specific polypropylene composition was heated from 60° C. to 220° C. at a rate of 20° C. per minute to produce a molten formulation and held at 220° C. for 2 minutes. At that time, the temperature was then lowered at a rate of 20° C. per minute until it reached the starting-temperature of 60° C. The crystallization temperature was thus measured as the peak maximum during the crystallization exotherm. The clarification performance of the nucleators was measured using ASTM D 1003-92.

The following Table lists haze and the peak crystallization temperatures for the plaques prepared in the manner described above.

TABLE 2

Experimental results for nucleators tested in formulations of Table 1.

| Additives | Additive Conc. (ppm) | % Haze | Polym. Cryst. Temp (Tc) (° C.) |
|---|---|---|---|
| Example 1 | 750 | 15.5 | 114.7 |
| Example 1 | 1500 | 15.1 | 114.7 |
| Example 2 | 1500 | 13.5 | 115.8 |
| Example 3 | 1500 | 18.2 | 109.2 |
| Example 4 | 1500 | 15.8 | 114.0 |
| Example 5 | 1500 | 21.4 | 115.6 |
| Example 7 | 1500 | 16.4 | 114.6 |
| Example 8 | 1500 | 19.3 | 114.7 |
| Example 9 | 1500 | 17.9 | 115.0 |
| Example 10 | 1500 | 18.3 | 114.8 |
| Example 11 | 1500 | 20.6 | 113.5 |
| Example 12 | 1500 | 15.4 | 115.5 |
| Example 13 | 1500 | 20.2 | 110.7 |
| Example 14 | 1500 | 14.5 | 114.4 |
| Example 15 | 1500 | 17.5 | 113.1 |
| Example 16 | 1500 | 15.2 | 115.3 |
| Example 17 | 1500 | 22.3 | 113.1 |
| Example 18 | 1500 | 17.5 | 113.1 |
| Example 18 | 2500 | 14.1 | 115.5 |
| Example 19 | 1500 | 16.2 | 115.0 |
| Example 20 | 1500 | 20.9 | 113.2 |
| Example 21 | 1500 | 17.8 | 114.4 |
| Example 22 | 1500 | 19.2 | 115.6 |
| Comparative Examples | | | |
| sodium, bicyclo[2.2.1]heptane dicarboxylate | 1500 | 34.1 | 112.8 |
| Control | 0 | 45.8 | 99.7 |

The data in Table 2 show that inventive nucleators exhibit generally significantly better haze performance than comparable sodium bicyclo[2.2.1]heptane dicarboxylate. Furthermore, polymer peak crystallization temperature is also higher for most of the inventive nucleators, when compared to the comparable example, sodium bicyclo[2.2.1]heptane dicarboxylate.

Some of the inventive nucleators were also tested in homopolymer polypropylene (12 MFR). The composition formulation is as follows:

TABLE 3

Homopolymer Polypropylene Composition

| Component | Amount |
|---|---|
| Polypropylene homopolymer (Himont Profax ® HP6301) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Nucleator | as noted |

The rest of the experimental procedures or conditions are same as in random copolymer polypropylene, and so are the measurement methods of haze and Tc. The performance of the inventive nucleates is shown in Table 4, below.

TABLE 4

Experimental results of inventive nucleators tested in formulations shown in Table 3.

| Additives | Additive Conc. (ppm) | % Haze | Polym. Cryst. Temp (Tc) (° C.) |
|---|---|---|---|
| Example 2 | 1500 | 16.4 | 127.5 |
| Example 5 | 1500 | 27.3 | 127.1 |
| Example 6 | 1500 | 32.5 | 126.3 |
| Example 21 | 1500 | 25.8 | 127.9 |
| Example 22 | 1500 | 20.7 | 127.2 |
| Comparative Examples | | | |
| sodium, bicyclo[2.2.1]heptane dicarboxylate | 1500 | 30.9 | 125.9 |
| Control | 0 | 58.4 | 114.7 |

Results from Table 4 show that the inventive nucleates provide generally improved optical performance than the comparative example, sodium, bicyclo[2.2.1]heptane dicarboxylate. Furthermore, the inventive nucleators exhibit improved polymer peak crystallization temperature.

Some inventive nucleators were also tested in a linear low density polyethylene (LLDPE), the grade used is Dowlex 2517, a Dow resin with 25 MFI, and 0.917 g/ml density. Similar processing conditions were used as in polypropylene resins. Haze and polymer Tc were measured the same way as in polypropylene. Composition of the formulation is shown in Table 5.

TABLE 5

LLDPE Composition

| Component | Amount |
|---|---|
| LLDPE (Dowlex 2517) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Nucleator | as noted |

Results of the test are shown in Table 6.

TABLE 6

Experimental results of inventive nucleators tested in formulations shown in Table 5.

| Additives | Additive Conc. (ppm) | % Haze | Polym. Cryst. Temp (Tc) (° C.) |
|---|---|---|---|
| Example 2 | 1500 | 71.0 | 107.1 |
| Example 12 | 1500 | 60.4 | 107.2 |
| Example 20 | 1500 | 50.5 | 107.2 |
| Comparative Examples | | | |
| sodium, bicyclo[2.2.1]heptane dicarboxylate | 1500 | 66.8 | 106.6 |
| Control | 0 | 94.1 | 101.2 |

The inventive nucleators generally outperform the comparable example in haze and polymer peak crystallization temperature in the LLDPE resin. A lower % haze is more desirable, and a higher Tc is more desirable, and the inventive nucleators perform generally more favorably in with regard to both % haze and Tc, as a general proposition.

The inventive compounds are generally more effective in terms of nucleating and clarifying capability in polyolefin resins, when compared to the base structure of sodium, bicyclo[2.2.1]heptane dicarboxylate. Several methods have been disclosed herein to achieve such improved performance.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

The invention claimed is:

1. A compound as shown in formula (I):

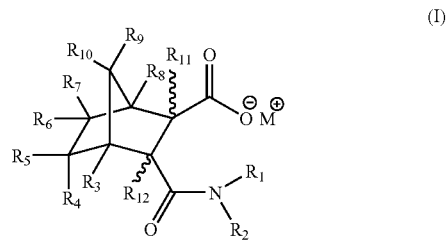

(I)

wherein M is a cation selected from the group consisting of: proton, metal cations, and organic cations, R1 and R2 are independently selected from the group consisting of: hydrogen, C1-C30 alkyl, C1-C30 alkenyl, C1-C30 alkynyl, C1-C30 alkoxy, hydroxy, aryl, alkylaryl, arylalkyl, polyoxyalkyl, polyaminoalkyl, and alkylsilyl, further wherein R1 and R2 may optionally form together C2-C9 alkylene carbocyclic or C2-C9 alkylene carbocyclic containing nitrogen and/or oxygen, and $R_3$, $R_4$, $R_5$, $R_6$, $R_7$, $R_8$, $R_9$, $R_{10}$, $R_{11}$, and $R_{12}$ are independently selected from the group consisting of: hydrogen, $C_1$-$C_9$ alkyl, hydroxy, $C_1$-$C_9$ alkoxy, amine, $C_1$-$C_9$ alkylamine, halogen, alkylphenyl, and phenyl, further wherein two vicinal or geminal $C_1$-$C_9$ alkyl groups may be combined to form a carbocyclic ring of up to six carbon atoms.

2. The compound of claim 1 wherein said M comprises a cation selected from the group of: sodium, calcium, zinc, potassium, and proton.

3. The compound of claim 1 wherein said $R_1$ and $R_2$ each are independently selected from $C_1$-$C_9$ alkyl groups.

4. The compound of claim 1 wherein said $R_1$ and $R_2$ each are selected independently from the group of: isobutyl, isopropyl, ethyl, and butyl.

5. The compound of claim 1 wherein said M comprises sodium and wherein said $R_1$ and $R_2$ comprise isobutyl.

6. The compound of claim 1 wherein said M comprises potassium and wherein said $R_1$ and $R_2$ comprise isobutyl.

7. The compound of claim 1 wherein said M comprises zinc and wherein said $R_1$ and $R_2$ comprise isobutyl.

* * * * *